US005625137A

United States Patent [19]

Madsen et al.

[11] Patent Number: 5,625,137
[45] Date of Patent: Apr. 29, 1997

[54] VERY LOW SCATTER LIQUID AND SOLID TISSUE MIMICKING MATERIAL FOR ULTRASOUND PHANTOMS AND METHOD OF MAKING THE SAME

[75] Inventors: Ernest L. Madsen; Gary R. Frank, both of Madison, Wis.

[73] Assignee: Wisconsin Alumni Research Foundation, Madison, Wis.

[21] Appl. No.: 449,755

[22] Filed: May 25, 1995

[51] Int. Cl.$^6$ .......................... G01N 37/00; G01N 29/06
[52] U.S. Cl. ...................... 73/1.84; 73/866.4; 252/315.1
[58] Field of Search .................... 73/1 DV, 1 R, 73/866.4, 644; 367/13; 436/8; 434/262, 270–274, 267; 252/315.1, 315.2, 315.3, 315.4, 408.1; 128/660.01, 660.06; 424/9.1, 9.5, 9.51, 9.52

[56] References Cited

U.S. PATENT DOCUMENTS

| | | | |
|---|---|---|---|
| 4,002,221 | 1/1977 | Buchalter | 73/644 X |
| 4,116,040 | 9/1978 | Skoknecht et al. | 73/1 DV X |
| 4,277,367 | 7/1981 | Madsen et al. | 252/408 |
| 4,286,455 | 9/1981 | Ophir et al. | 73/1 DV |
| 4,323,077 | 4/1982 | Smith | 128/660.01 |
| 4,331,021 | 5/1982 | Lopez et al. | 73/1 DV |
| 4,406,153 | 9/1983 | Ophir et al. | 73/1 DV |
| 4,453,408 | 6/1984 | Clayman | 73/1 DV |
| 4,466,442 | 8/1984 | Hilmann et al. | 128/662.02 X |
| 4,681,119 | 7/1987 | Rasor et al. | 128/660.01 X |
| 4,843,866 | 7/1989 | Madsen et al. | 73/1 DV |
| 5,054,310 | 10/1991 | Flynn | 73/1 DV |
| 5,310,540 | 5/1994 | Gidday et al. | 128/660.01 X |
| 5,312,755 | 5/1994 | Madsen et al. | 436/8 |
| 5,352,436 | 10/1994 | Wheatley et al. | 128/660.02 X |
| 5,456,901 | 10/1995 | Unger | 128/662.02 X |

OTHER PUBLICATIONS

Goldstein, et al. May (1983), "Particle Image–resolution Test Object", *J. Ultrasound Med.*, vol. 2, pp. 195–209.
Goodsitt, et al. (1983), "A Three Dimensional Model for Generating the Texture in B–scan Ultrasound Images", *Ultrasonic Imaging*, 5, pp. 253–272 of pp. 253–279.
Madsen, et al. (1982), "An Anthropomorphic Ultrasound Breast Phantom Containing Intermediate–Sized Scatterers", *Ultrasound in Med. and Biol.*, vol. 8, No. 4, pp. 381–392.
Madsen, et al. Feb. (1982), "Anthropomorphic Breast Phantoms for Assessing Ultrasonic Imaging Systems Performance and for Training Ultrasonographers Part I", *J. Clin. Ultrasound*, vol. 10, No. 2 pp. 67–75.

(List continued on next page.)

*Primary Examiner*—Thomas P. Noland
*Attorney, Agent, or Firm*—Foley & Lardner

[57] ABSTRACT

A tissue mimicking material for use in ultrasound scanner phantoms has a very low acoustic backscatter coefficient. The tissue mimicking material has the ultrasonic speed and attenuation characteristics of human tissue, with a backscatter coefficient of about 40 dB below that of human liver tissue. The tissue mimicking material may be in liquid or solid form. A component in both the liquid and solid forms is a filtered aqueous mixture of large organic water soluble molecules and emulsion of fatty acid esters. This mixture may be based on a combination of evaporated whole milk and water. The material also includes a hydroxy compound, such as n-propanol, to control the ultrasonic speed of propagation through the material. A preservative from bacterial invasion, such as thimerosal, is also preferably included in the material. The solid form of the material contains the same material as the liquid form, with a very pure gel-forming material included to form a solid material. The tissue mimicking material may be included in an ultrasound phantom container with solid scattering particles and/or test objects incorporated therein. The use of scattering particles allows a very broad range of relative backscatter levels to be achieved in ultrasound test object phantoms incorporating the tissue mimicking material of the invention.

27 Claims, 2 Drawing Sheets

OTHER PUBLICATIONS

Madsen, et al. Mar. (1982), "Anthropomorphic Breast Phantoms for Assessing Ultrasonic Imaging Systems Performance and for Training Ultrasonographers Part II", *J. Clin. Ultrasound*, vol. 10, No. 3 pp. 51–100.

Madsen, et al. Sep. (1984), "Method of data reduction for accurate determination of acoustic backscatter coefficients", *J. Acoust. Soc. Am.*, vol. 76, No. 3, pp. 913–923.

Smith, S. W. and H. Lopez "A contrast–detail analysis of diagnostic ultrasound imaging", *Med. Phys.*, vol. 9, No. 1, pp. 4–12, Jan./Feb. 1982.

Translation of German patent application publication No. 2814336.

"What a Hospital Physicist Needs in a Transducer Characterization Standard: Are Tissue Equivalent Test Objects Necessary?" *IEEE Transactions on Sonics and Ultrasonics* vol. S U–26, No. 1, Jan. 1979, pp. 1–6 by Paul L. Carson.

*Patent Abstracts of Japan* Grp. P. 860 vol. 13, No. 165, Abs pub. date Apr. 20, 1989 (1–3558) "Coupling Medium for Non–Destructive Inspection".

VERY LOW SCATTER LIQUID AND SOLID TISSUE MIMICKING MATERIAL FOR ULTRASOUND PHANTOMS AND METHOD OF MAKING THE SAME

FIELD OF THE INVENTION

This invention pertains generally to the field of materials which closely mimic the ultrasonic propagation characteristics of human tissue, and particularly to such materials used in ultrasound phantoms for use with ultrasound scanners.

BACKGROUND OF THE INVENTION

Materials which closely mimic the ultrasonic propagation characteristics of human tissue are employed in imaging phantoms and other test objects for use with ultrasound scanners. These phantoms may be used to carry out performance checks on ultrasound scanners. Phantoms may also be used for training or testing student technologists in the operation of ultrasound scanners or the interpretation of ultrasound images produced by such scanners.

Ideally, such material should be capable of mimicking soft human tissue with respect to at least three characteristics: speed of sound, ultrasonic attenuation, and ultrasonic scattering. The speed of sound in the tissue mimicking material should rest in the range from approximately 1460 m/s, characteristic of human fat tissue, to 1640 m/s, characteristic of the human eye's lens. The attenuation coefficient with respect to frequency of the material should lie in the range from approximately 0.4 dB/cm/MHz, characteristic of human fat tissue, to 2.0 dB/cm/MHz, characteristic of human muscle tissue. Additionally, the attenuation coefficient should be approximately proportional to the ultrasonic frequency. In other words, the attenuation coefficient with respect to frequency, or the attenuation coefficient slope, should remain constant for varying ultrasonic frequencies. These characteristics of human tissue should be maintained at all frequencies in the typical range of ultrasonic scanners, from 1–10 MHz. Moreover, the variation of these characteristics within the range of room temperature should be small. Additionally, these materials should be stable in time and invulnerable to reasonable environmental fluctuations. They should also be free of any pockets of air or gas. Furthermore, the bulk properties of the material should be the same throughout the volume of a particular phantom or phantom section.

A tissue mimicking material satisfying the above characteristics was disclosed in U.S. Pat. No. 4,277,367, to Madsen, et al., entitled Phantom Material and Method, the disclosure of which is incorporated herein by reference. In that patent it was disclosed that both the speed of sound and the ultrasonic attenuation properties, matching those of most soft tissues, could be simultaneously controlled in a mimicking material based on water based gels, such as those derived from animal hides. It was disclosed that pharmaceutical gels could be made to mimic human soft tissue from the standpoint of attenuation coefficient by having a uniform distribution of graphite powder in the gel, and that the magnitude of the attenuation coefficient could be controlled by varying the concentration of graphite. The speed of sound in such a gel suspension could be varied between 1560–1700 m/s at room temperature and was independent of the graphite concentration. The attenuation coefficient was also nearly proportional to the frequency. In one embodiment of that invention, ultrasound phantoms embodying the desired features for mimicking soft tissue were prepared from a mixture of gelatin, water, n-propanol and graphite powder, with a preservative. In another embodiment, an oil and gelatin mixture formed the basis of the tissue mimicking material.

Tissue mimicking material is typically used to form the body of an ultrasound scanner phantom. This is accomplished by enclosing the material in a container which is closed by an ultrasound transmitting window cover. The tissue mimicking material is admitted to the container in such a way as to exclude air bubbles from forming in the container. In addition to the tissue mimicking material itself, scattering particles, spaced sufficiently close to each other that an ultrasound scanner is incapable of resolving individual scattering particles, and testing spheres or other targets may be located within the phantom container, suspended in the tissue mimicking material body. Such an ultrasound phantom is useful in evaluating the ability of ultrasound medical diagnostic scanners to resolve target objects of selected sizes located throughout the tissue mimicking material. The objective is for the ultrasound scanner to resolve the testing spheres or other targets from the background material and scattering particles. This type of ultrasound phantom is described in U.S. Pat. No. 4,843,866, to Madsen, et al., entitled Ultrasound Phantom, the disclosure of which is incorporated herein by reference.

SUMMARY OF THE INVENTION

In accordance with the present invention, there is provided a tissue mimicking material for ultrasound phantoms having speed of sound and ultrasonic attenuation characteristics of human tissue, with very low ultrasonic scatter levels. The relative backscatter levels achieved by the tissue mimicking materials of the present invention are about 40 dB below the ultrasonic scatter level of human liver tissue, and about 25 dB below the scatter levels of prior tissue mimicking materials, such as that disclosed in U.S. Pat. No. 4,277,367. Such low scatter material allows for testing for side lobes in ultrasonic transducer acoustic pressure amplitude patterns. The controlled addition of solid scatterers to the solid type of tissue mimicking material allows relative backscatter levels to be achieved within a very broad range for use in phantoms used as ultrasound scanner test objects.

The tissue mimicking material of the present invention may be in liquid or solid form. The liquid form allows medical ultrasound scanner beam properties to be determined at arbitrary positions via immersing movable detectors or reflectors at various positions in a phantom containing the liquid material. The liquid form of the present invention also allows phantom test objects to be refilled with materials mimicking ultrasonically different parenchymal tissues. The liquid material may be formed of a filtered aqueous mixture of large organic water soluble molecules and an emulsion of fatty acid esters, an organic hydroxy compound and, preferably, a preservative to inhibit bacterial invasion. N-propanol is a preferred hydroxy compound, and thimerosal may be used as the preservative.

The solid form of the tissue mimicking material of the present invention allows a broad range of relative backscatter levels to be achieved in ultrasound phantoms by suspending solid scatterers of various sizes and concentrations throughout the phantom body tissue mimicking material. Target objects having different ultrasonic characteristics from the body tissue mimicking material may also be suspended in the phantom body. The solid material contains the same components as the liquid form, with a very pure gel-forming material such as gelatin, polyacrylamide gel, or agarose included to form an elastic solid material.

A component of both the liquid and solid forms is the filtered aqueous mixture of large organic water soluble molecules and an emulsion of fatty acid esters. This component may be made from a mixture of evaporated whole milk and water. The high purity gel-forming material is utilized for maintaining the solid form. The n-propanol or other hydroxy compound is important for controlling ultrasonic speed of propagation through the material.

The solid form of the tissue mimicking material of the present invention allows complex phantoms to be constructed. Such phantoms are constructed by placing the tissue mimicking material in a phantom container which is closed by an ultrasound transmitting window cover. Scatter particles and test objects, such as simulated tumors with different backscatter and/or other characteristics than the surrounding material, may be suspended throughout the tissue mimicking material enclosed in the container.

Further objects, features, and advantages of the invention will be apparent from the following detailed description when taken in conjunction with the accompanying drawings.

DETAILED DESCRIPTION OF THE INVENTION

Figure 1:
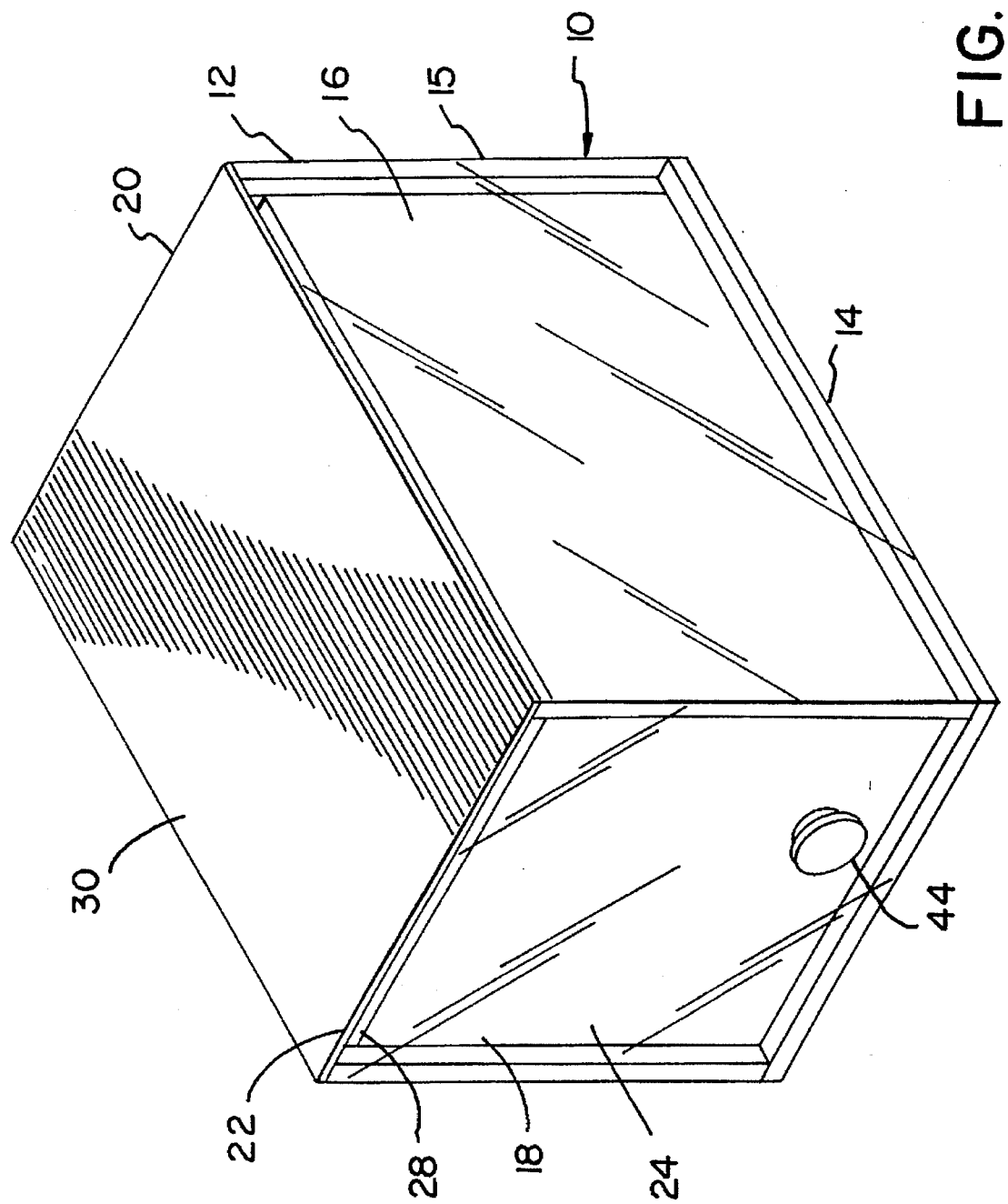
FIG. 1 is a perspective view of an ultrasound phantom containing the tissue mimicking material of the present invention.

The tissue mimicking material of the present invention includes a filtered aqueous mixture of large organic water soluble molecules and an emulsion of fatty acid esters. Very small particle size is important to achieving low backscatter levels. A tissue mimicking material in accordance with the present invention in liquid form contains the filtered aqueous mixture of large organic water soluble molecules and an emulsion of fatty acid esters and an organic hydroxy compound, which is important for controlling the ultrasonic speed of propagation through the material. A preservative against bacterial invasion is also preferably included in the material. An alcohol, such as n-propanol, is a preferred hydroxy compound and thimerosal is a preferred preservative.

The tissue mimicking material of the present invention, in liquid form, may be produced using the procedure of the following example. Commercially available evaporated homogenized whole milk and water may be used to form the filtered aqueous mixture of large organic water soluble molecules and an emulsion of fatty acid esters. Regular homogenized milk may also be used but the attenuation coefficient will be minimal, allowing little flexibility in its choice through dilution with water. The evaporated whole milk is first agitated and then poured into a beaker and warmed, in double boiler fashion, to 68° C. The warmed milk is then filtered to eliminate calcium particles from the evaporated milk. Preferably a filter paper is used which retains particles greater than 8 micrometers in diameter. A 9 cm diameter Whatman TM 540 hardened ashless paper filter in a vacuum filter apparatus connected to a Bernoulli vacuum outlet on a water pipe may be employed for the filtering step of this process. As an alternative to filtering, the calcium particles may be eliminated from the evaporated milk by allowing the milk to remain at rest, so gravity acts to pull the particles to the bottom of the milk container, and then pouring off the top part of the milk for use in the remaining steps. The tissue mimicking material of the present invention may be made without employing a filtering step at all, however, filtering is preferred. Three parts of the filtered evaporated milk, now at room temperature, are then combined with two parts of a degassed solution of deionized water and n-propanol. Degassing may be done by placing a beaker of the material to be degassed in a sufficiently large clean desiccator and applying a vacuum via a laboratory vacuum pump generating a minimum absolute pressure of 60 mmHg. This vacuum is mild enough that water will not boil at room temperature. The water is preferably deionized to 18 Megohm-cm. The resulting mixture is approximately 60% evaporated milk, 37% water, and 3% n-propanol by volume of components. At this point, 1 gram of thimerosal per liter of mixture may be added and mixed in. The mixture is then degassed for about 15 minutes, removed from the vacuum apparatus, and the bubble layer formed on the top of the mixture is removed. The mixture is then stirred well and poured into a phantom container where it is sealed from exposure to the air.

Other products similar to evaporated whole milk, such as coffee creamers like liquid Coffeemate or homogenized "half and half" may also form the basis of the filtered aqueous mixture of large organic water soluble molecules and emulsion of fatty acid esters. A combination of whipping cream and milk can provide a material having ultrasonic characteristics similar to human blood, including its low backscatter coefficient.

The liquid form of the tissue mimicking material of the present invention allows the beam properties of ultrasound medical equipment to be determined at arbitrary positions by immersing movable detectors or reflectors in the liquid tissue mimicking material enclosed in an ultrasound phantom. Additionally, test object phantoms can be refilled with liquid material which mimics ultrasonically different parenchymal tissues. For example, by altering the concentration of n-propanol in the material, materials with varying ultrasonic speed characteristics may be created.

A solid tissue mimicking material in accordance with the present invention contains the same components as the liquid form, with a very pure gel-forming material such as gelatin, polyacrylamide gel, or agarose included to form a solid material. A preferred gel-forming material is agarose. The high purity gel-forming material performs the function of maintaining a solid form with the liquid tissue mimicking components held therein without substantial settling or diffusion. This solid and stable gel structure allows complex phantoms to be constructed containing, e.g., simulated tumors with different backscatter characteristics than the surrounding phantom body material, as described in more detail below.

A solid type tissue mimicking material in accordance with the present invention may be produced using the following procedure. Once again, evaporated whole milk is used as the basis of the filtered aqueous mixture of large organic water soluble molecules and an emulsion of fatty acid esters which is the essential component of the material. Also, n-propanol is the preferred hydroxy compound used for controlling the ultrasonic speed of propagation through the material, and thimerosal is the preferred preservative. First, a solution of agarose is prepared (e.g., approximately 500 cc). A suitable agarose produced by Sigma Chemical is electrophoresis reagent EE 0.10–0.15.40 cc of n-propanol and 460 cc of deionized water are mixed at room temperature in a Pyrex beaker. 20 grams of dry agarose are added and the mixture is heated in a double boiler until the solution is transparent. This occurs at a solution temperature of about 90° C. The temperature of the solution is reduced to 60° C. and 450 cc of filtered evaporated milk, also at 60° C., are added to the agarose solution. The evaporated milk may be filtered by the method described above for the liquid type tissue mimicking material. Thimerosal, 0.9 grams, is then added to the solution which is stirred well. The solution is then cooled to 50° C. by immersing the lower part of the beaker in a cold tap water bath and stirring the mixture. The still molten material is then poured into a phantom container where it is sealed from air. The phantom container may be clamped onto an apparatus for rotating the phantom at about 2 rpm about a horizontal axis. The phantom is preferably allowed to rotate overnight to assure congealing of the tissue mimicking material without gravitational sedimentation.

The resulting solid tissue mimicking material has been found to have the following ultrasonic properties at 22° C. The ultrasonic speed is approximately 1538 m/s, which is very near the mean ultrasonic speed of human tissue, 1540 m/s, assumed in the use of typical medical ultrasound scanners. This ultrasonic speed can be easily raised or lowered by increasing or decreasing the hydroxy (in this case n-propanol) concentration of the material. As is shown in Table 1, the ultrasonic attenuation characteristics of the solid tissue mimicking material are also consistent with the ultrasonic characteristics of human tissue. Note that the attenuation coefficient is approximately proportional to the ultrasonic scanning frequency across selected frequencies in the clinical ultrasound scanner range.

TABLE 1

| Attenuation Characteristics of Low Scatter Material | | |
|---|---|---|
| Frequency (MHz) | Attenuation (dB/cm) | Atten. Coeff. Slope (dB/cm/MHz) |
| 2.50 | 1.15 | 0.46 |
| 4.50 | 2.27 | 0.50 |
| 6.20 | 3.09 | 0.50 |
| 8.00 | 4.03 | 0.50 |

Most significantly, the backscatter coefficient of the solid tissue mimicking material is much lower than that attainable with materials presently used in ultrasound phantoms. The backscatter coefficient is found to be at about 25 dB below the lowest backscatter material producible using the formulation disclosed in U.S. Pat. No. 4,277,367. This is approximately 40 dB below the backscatter level of human liver tissue. The level is, for present purposes, essentially negligible.

The low backscatter coefficient of the tissue mimicking material of the present invention was determined by direct imaging comparisons on an ultrasound scanner. An image of the brightness echo pattern of a sample of prior art tissue mimicking material containing graphite powder was produced on one side of an ultrasound display monitor. Using the same instrument settings, an echo pattern image of the very low scatter material of the present invention was produced on the other side of the monitor. The imaged echo level brightnesses were then made about the same by adjusting the electronic gain applied to the echoes. The electronic gains were displayed on the monitor. In one test, the gain applied for the graphite containing sample was −10 dB and that for the very low scatter material was +15 dB for a total difference of 25 dB.

An ultrasound scanner phantom incorporating the tissue mimicking material of the present invention is shown generally at 10 in FIG. 1. The ultrasound phantom 10 includes a container 12 having a bottom 14 and walls 15. Preferably the walls 15 include opposed faces 16, and opposed ends 18. Taken together, the bottom, faces, and ends 14, 16, and 18 form a hollow, box-like container structure. Margins of the walls 15 remote from the bottom 14 define a window 20. The window 20 is closed with an ultrasound-transmitting window cover 22. The window cover 22 may be made of any cohesive ultrasound transmitting material of suitable physical durability. A thin sheet of polyurethane or saran is preferred.

The ultrasound phantom 10 further includes a body 24 of the tissue mimicking material of the present invention. This material substantially fills the container 12 up to the level of the window 20, except as shall be discussed below. The phantom body 24 includes the tissue mimicking material of the present invention 26. As discussed above, the material 26 has attenuation and ultrasonic speed characteristics of human tissue combined with a very low ultrasonic backscatter coefficient.

Solid scattering particles may be added to the solid form of phantom body 24 such that their presence increases the backscatter coefficient of the tissue mimicking material 26 to a selected level. The liquid version of the material is not capable of maintaining a uniform suspension of solid scattering particles because of the great difficulty of precisely matching specific gravities of liquid and solid scatterers. To be effective, a scattering particle must be large enough so that measurable ultrasonic scatter occurs and small enough and sufficiently closely spaced that the texture pattern displayed by the ultrasound scanner being tested does not represent resolution of individual scattering particles. Any material that differs from the tissue mimicking material 26 in specific gravity and/or ultrasonic speed is capable of causing scatter. Glass beads have been found acceptable for use as scattering particles, with the diameters of the glass beads being not less than 40 microns and not greater than 100 microns. Preferably these solid scattering particles may be included in the solid type tissue mimicking material of the present invention by adding 45–53 micron diameter glass beads at a concentration of a few grams per liter to the tissue mimicking material, prior to cooling the mixture and before congealing. Allowing the phantom to rotate overnight, to assure congealing without gravitational sedimentation, is particularly important when such scatterers have been added and sedimentation of the glass beads might occur.

The tissue mimicking material of the present invention contains water and is subject to drying by escape of the water to the atmosphere. This can result in changes in acoustic properties that make the material a less effective tissue mimicker. Consequently, the container 12 must be liquid tight and preferably also water vapor tight. The window cover 22 must include means for reducing water transfer therethrough. To this end, the window cover 22 may be made of a flexible plastic material that does not readily transmit water vapor. An alternative means for reducing water transfer through the window cover 22 includes a layer 28 of an oil-based gel that completely closes the window 20, adhering to the uppermost portions of the faces 16 and ends 18 in water and water vapor tight relation. The layer 28 of oil-based gel preferably is also covered with a thin and flexible plastic sheet 30 that serves to form and protect the surface of the layer 28 of oil-based gel.

In practice, the bottom 14, faces 16, and ends 18 may be molded as a unit or formed of flat pieces of plastic or other material and be glued or otherwise joined so as to constitute the container 12. If the window cover 22 is to include the layer of oil-based gel, the plastic sheet 30 may first be glued or otherwise attached to the container 12 so as to close the window 20 in liquid-tight relation. At least one of the bottom 14, faces 16, or ends 18 includes a filling hole, shown at 32 and located in an end 18 of the ultrasound phantom 10 shown in FIG. 1 and FIG. 2. The layer 28 of oil-based gel may then be created by inserting through the filling hole 32 a sufficient quantity of the oil-based gel to make the layer 28, the oil-based gel so inserted being in molten form. With the container 12 oriented so that the window 20 is downward most, the molten oil-based gel may then be allowed to cool and solidify. The exact thickness of the layer 28 is not critical.

After the layer 28 of oil-based gel has been formed, the remainder of the container 12 may be filled with the tissue mimicking material 26 by inserting the material in liquid form through the filling hole 32 and, for the solid form, allowing it subsequently to solidify as described above. It is important that the tissue mimicking material 26 completely fill the space remaining in the container 12 beneath the level of the layer 28 of oil-based gel, with no air bubbles remaining. Any of a number of convenient techniques may be utilized to accomplish this end. It is convenient to utilize a filling syringe, shown in cross-section in FIG. 2 at 34. The filling syringe 34 may be any conventional syringe with a barrel 36, plunger 38 and plunger seal 40. The portion of the barrel 36 that would normally be adapted to receive a needle may be cut off to leave the barrel open-ended. The filling syringe 34 is selected to have a size sufficiently large that the barrel 36 may be attached to the end 18 in which the filling hole 32 is located, with the barrel entirely surrounding and thus closing the filling hole 32.

Figure 2:
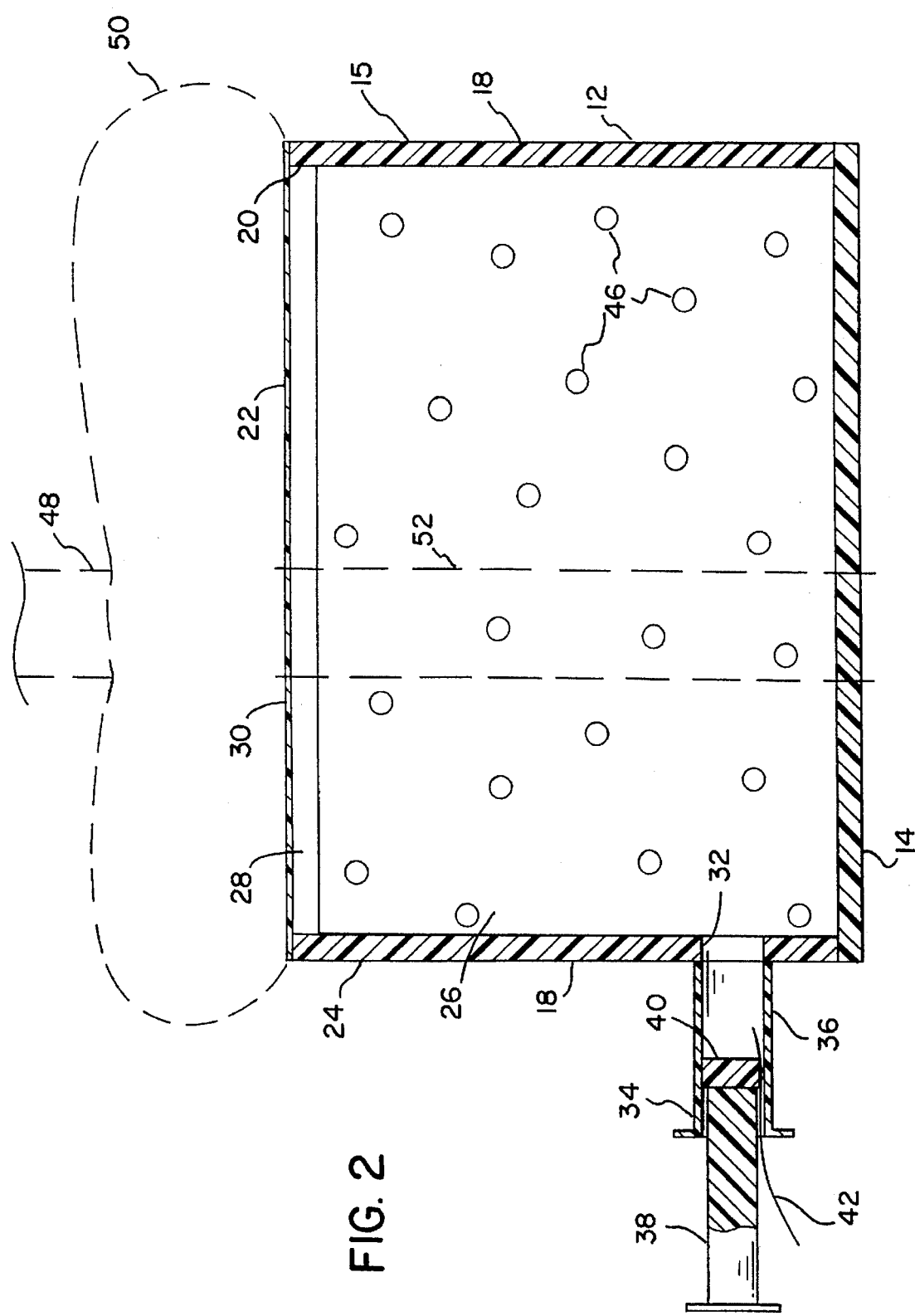
FIG. 2 is a cross-sectional view of an ultrasound phantom similar to the phantom shown in FIG. 1, showing testing spheres suspended throughout the tissue mimicking material enclosed in the phantom. The testing spheres suspended in the tissue mimicking material are not shown to scale or in numbers accurately reflecting their concentration within the phantom body.

When the tissue mimicking material 26 is inserted through the filling hole 32, as described above, it is inserted through the barrel 36 of the filling syringe 34, with the plunger 38 removed. The material is allowed also to fill part of the barrel 36. With the material still in its molten form, the plunger 38 is reinserted into the barrel 36 with a strand of wire, such as is shown in FIG. 2 at 42, inserted beside the plunger 38 to extend past the plunger seal 40 into the barrel 36. The wire 42 distorts the plunger seal 40 sufficiently that air bubbles and any excess liquid tissue mimicking material 26 may escape past the plunger seal 40. The filled container 12 may be manually rotated and shaken so as to direct all air bubbles contained therein up into the barrel 36 of the filling syringe 34 and further up against the plunger seal 40 near the position of the wire 42. By application of pressure to the plunger 38, any such air bubbles may be forced past the plunger seal 40 at the point where the wire 42 has distorted the plunger seal. By this means, the container 12 may be entirely filled, with all air bubbles removed. The wire 42 may then be pulled out of the barrel 36 from the plunger 38 side, whereupon the plunger seal 40 prevents the readmission of any air to the container 12. Relative to the solid material, after the material 26 has solidified, which preferably occurs during a rotation of the phantom as described above, the filling syringe 34 may be removed from the container 12 and the filling hole 32 closed by any convenient means, such as the stopper shown in FIG. 1 at 44.

The phantom body 24 may contain, in addition to the solid tissue mimicking material 26, testing spheres 46. This important version of the phantom may be referred to as a "lesion detectability phantom". In this type of phantom, it is necessary that the ultrasonic speed of propagation and attenuation coefficient slope be the same everywhere in the phantom body 26 with the only variable being the backscatter coefficient over the small, lesion-like, spherical target volumes.

The testing spheres 46 may be made of the tissue mimicking material of the present invention, and may, therefore, have the same ultrasonic speed and attenuation characteristics of the rest of the material 26 in the phantom body 24. However, the testing spheres 46 must then have a backscatter coefficient or other characteristics different from that of the other material 26. The testing spheres 46, therefore, may most conveniently be made of the tissue mimicking material of the present invention with a different concentration of scattering particles, such as glass beads, than in the body material 26.

If the glass bead concentration is the same in the test lesions 46 as in the tissue mimicking material surrounding them 26, then the lesions are not detectable in ultrasound images because there is no backscatter contrast. Contrast is attained by having a different concentration of glass beads in the lesions than in their surroundings. The concentration of 40 micrometer diameter glass beads in the surroundings must be about 8 grams per liter so that the backscatter is representative of commonly scanned organ parenchymae such as liver.

The weakness of prior art tissue mimicking materials, containing graphite powder to control ultrasonic absorption (attenuation), is that the powdered graphite gives rise to a somewhat unpredictable low level of backscatter, in addition to the dominating absorption. Thus, in test lesions made of the prior art material containing no glass beads, there will be an unpredictable contrast somewhere between −18 dB and −14 dB for the lesions relative to the surroundings. Thus, production of lesions with a predictable contrast of −10 db or lower is not possible with the prior art material, because the contribution to the backscatter by the graphite is neither negligible nor predictable. Also, the most negative contrast value is limited to −14 to −18 dB. As mentioned above, however, the backscatter level of the tissue mimicking material of the present invention is essentially negligible. Thus, complete predictability exists because all significant backscatter is due to the added glass beads. For example, if the concentration of beads in the surroundings is 8 grams per liter, then 1 gram per liter yields −9 dB, 0.5 grams per liter yields −12 dB, 0.25 grams per liter yields −15 dB, etc., and these values are completely predictable. Moreover, due to the very low scatter characteristics of the tissue mimicking material of the present invention, extreme differences in backscattering coefficients can be obtained when no backscattering particles are used in the testing spheres, and a concentration of scattering particles giving rise to backscatter characteristics of normal tissue are used in the body material 26, or vice versa.

The testing spheres 46 may be made of the solid tissue mimicking material of the present invention by molding in a two-part, split mold of conventional design (not shown). If necessary in order to distribute any attenuation or scattering particles uniformly through the testing spheres 46, the filled mold may be rotated as the testing spheres solidify. The testing spheres 46 may be mixed with the body material 26 prior to filling of the container 12. With the container filled, it may be vigorously shaken and agitated with a rotational motion to assure a random distribution of the testing spheres before the tissue mimicking body material 26 begins to solidify. When the body material 26 has solidified, the testing spheres 46 are embedded within it, distributed throughout the phantom body 24 in a random array, or at least in unpredictable locations therein.

The diameter of the testing spheres 35 is selected to be of a size appropriate for testing the resolution abilities of an ultrasound scanner having an ultrasound scanning head, such as that shown in FIG. 2 at 48. The ultrasound scanning head 48 may either be directly applied to the window cover 22, or, as is shown in FIG. 2, may be equipped with a water bag 50 or any of the other spacers or surface conformation arrangements commonly used with diagnostic and other ultrasound scanning heads. As is well known to those skilled in the art, an ultrasound scanning head may be used to scan a space below it commonly referred to as a slice, indicated in FIG. 2 at 52. Any ultrasound scanning head has a zone within the slice being scanned within which it achieves resolution of objects of a given size and acoustical characteristics. No matter what size of testing sphere 46 is employed, it will be apparent that the phantom 10 may be used to demonstrate the ability of the ultrasound scanning head 48 to resolve spheres of that size at any given location within the slice 52. Furthermore, the phantom 10 can be used to demonstrate the ability of the ultrasound scanner to so detect the testing spheres 46 when they differ from the tissue mimicking body material 26 in backscatter coefficient or other ultrasound acoustical property to any selected extent. The advantages of unpredictable locations of the testing spheres 46 within the phantom body 24 are described in U.S. Pat. No. 4,843,866, incorporated herein by reference.

The ultrasound scanner phantom described above is only one of many embodiments of ultrasound scanner phantoms which may incorporate the tissue mimicking material of the present invention. Many other materials, arrangements of parts, and modes of assembly are possible. Many other target shapes besides testing spheres may be embedded in the tissue mimicking material. For example, line targets, of nylon or stainless steel, may be used. The target objects may be also cone-shaped, or stepped cylinders. Alternatively, spherical targets may be included in the tissue mimicking material which are distributed in a defined pattern, rather than randomly, throughout a phantom body. Also, the phantom body may be divided into two or more subsections, each subsection having the tissue mimicking material of the present invention with different concentrations of scattering particles, or different targets, embedded therein. A more detailed description of the construction and use of such phantoms may be found in U.S. Pat. No. 4,843,866.

It is understood that the present invention is not limited to the particular embodiments or processes described herein for illustration, but it embraces all such modified forms thereof as come within the scope of the following claims.

What is claimed is:

1. A low scatter ultrasound tissue mimicking material comprising: an aqueous mixture of large organic water soluble molecules and an emulsion of fatty acid esters mixed with a hydroxy compound soluble in water.

2. The tissue mimicking material of claim 1 wherein the aqueous mixture is filtered.

3. The tissue mimicking material of claim 1 wherein the hydroxy compound is n-propanol.

4. The tissue mimicking material of claim 1 additionally comprising a preservative mixed with the aqueous mixture and the hydroxy compound.

5. The tissue mimicking material of claim 4 wherein the preservative is thimerosal.

6. The tissue mimicking material of claim 1 additionally comprising a gel-forming material mixed with the aqueous mixture and the hydroxy compound.

7. The tissue mimicking material of claim 6 wherein the gel-forming material is selected from the group consisting of very pure gelatin, polyacrylamide gel, and agarose.

8. The tissue mimicking material of claim 6 additionally comprising solid scattering particles in the mixture.

9. The tissue mimicking material of claim 8 wherein the solid scattering particles are glass beads.

10. A low scatter ultrasound tissue mimicking material comprising: an aqueous mixture of large organic water soluble molecules and an emulsion of fatty acid esters mixed with a hydroxy compounds soluble in water and wherein the aqueous mixture is made from evaporated whole milk and water.

11. The tissue mimicking material of claim 10 wherein the evaporated milk is approximately 60% by volume of the tissue mimicking material, water is approximately 37% by volume of the tissue mimicking material, and n-propanol is approximately 3% by volume of the tissue mimicking material.

12. The tissue mimicking material of claim 10 comprising additionally thimerosal in an amount approximately 0.1% by weight of the tissue mimicking material.

13. A low scatter tissue mimicking material, comprising a mixture of evaporated whole milk, deionized water, agarose, and n-propanol.

14. The tissue mimicking material of claim 13 additionally comprising thimerosal added to the mixture as a preservative.

15. The tissue mimicking material of claim 13 additionally comprising solid scattering particles in the mixture.

16. The tissue mimicking material of claim 15 wherein the solid scattering particles are glass beads.

17. An ultrasound phantom for use with an ultrasound scanner, comprising:
   (a) a container having a bottom and walls, margins of the walls remote from the bottom defining a window, which is closed by an ultrasound-transmitting window cover; and
   (b) a phantom body contained within the container and including a low scatter tissue mimicking material, comprising an aqueous mixture of large organic water soluble molecules and an emulsion of fatty acid esters mixed with a hydroxy compound soluble in water and a gel-forming material.

18. The ultrasound phantom of claim 17 wherein the aqueous mixture is filtered.

19. The ultrasound phantom of claim 17 wherein the hydroxy compound is n-propanol.

20. The ultrasound phantom of claim 17 wherein the phantom body additionally includes a preservative.

21. The ultrasound phantom of claim 20 wherein the preservative is thimerosal.

22. The ultrasound phantom of claim 17 wherein the gel-forming material is selected from the group of gel-forming materials consisting of very pure gelatin, polyacrylamide gel, or agarose.

23. The ultrasound phantom of claim 17 wherein the phantom body additionally includes solid scattering particles.

24. The ultrasound phantom of claim 23 wherein the solid scattering particles are glass beads.

25. The ultrasound phantom of claim 17 wherein the phantom body additionally includes a multiplicity of testing spheres having a testing sphere ultrasonic speed, attenuation coefficient, and backscatter coefficient, at least one of which is different from a corresponding tissue mimicking material ultrasonic speed, attenuation coefficient, and backscatter coefficient of the tissue mimicking material.

26. The ultrasound phantom of claim 25 wherein the testing spheres are located within the phantom body in a random and unpredictable array.

27. An ultrasound phantom for use with an ultrasound scanner, comprising:

(a) a container having a bottom and walls, margins of the walls remote from the bottom defining a window, which is closed by an ultrasound-transmitting window cover; and (b) a phantom body contained within the container and including a low scatter tissue mimicking material, comprising an aqueous mixture of large organic water soluble molecules and an emulsion of fatty acid esters mixed with a hydroxy compound soluble in water and gel-forming material and wherein the aqueous mixture is made from evaporated whole milk and water.

* * * * *

UNITED STATES PATENT AND TRADEMARK OFFICE
CERTIFICATE OF CORRECTION

PATENT NO.   :   5,625,137
DATED        :   April 29, 1997
INVENTOR(S)  :   Madsen, et al.

It is certified that error appears in the above-indentified patent and that said Letters Patent is hereby corrected as shown below:

In column 10, line 11 of the patent, delete "compounds" and insert --compound--

In column 12, line 5 of the patent, after "and" insert --a--

Signed and Sealed this

Fifth Day of January, 1999

*Attest:*

*Attesting Officer*          *Acting Commissioner of Patents and Trademarks*